United States Patent [19]

Epstein

[11] Patent Number: 5,020,526

[45] Date of Patent: Jun. 4, 1991

[54] EYE BOTTLE

[76] Inventor: David L. Epstein, 14 Glezen La., Wayland, Mass. 01778

[21] Appl. No.: 310,480

[22] Filed: Feb. 13, 1989

Related U.S. Application Data

[63] Continuation of Ser. No. 16,538, Feb. 19, 1987, abandoned.

[51] Int. Cl.$^5$ ............................................. A61M 11/00
[52] U.S. Cl. .......................... 128/200.14; 128/200.19; 604/295; 604/300
[58] Field of Search .................... 128/200.14, 200.19, 128/200.23; 604/281-283, 257, 261, 294-302

[56] References Cited

U.S. PATENT DOCUMENTS

| | | | |
|---|---|---|---|
| 1,574,575 | 2/1926 | Harmon et al. | 604/261 |
| 1,655,678 | 1/1928 | Dorment | 128/200.14 |
| 1,765,114 | 6/1930 | Turner | 604/295 |
| 1,855,653 | 4/1932 | Strauss | 604/295 |
| 2,980,342 | 4/1961 | Armour | 128/200.14 |
| 3,116,856 | 1/1964 | Prussin et al. | 128/200.23 |
| 3,148,806 | 9/1964 | Meshberg | 128/200.23 |
| 3,308,999 | 3/1967 | Darlington, Jr. | 604/294 |
| 3,506,001 | 4/1970 | Costello | 604/294 |
| 3,640,274 | 2/1972 | Costello | 128/200.14 |
| 3,666,182 | 5/1972 | Cureton | 128/200.14 |
| 4,363,323 | 12/1982 | Geiss | 604/281 |
| 4,550,866 | 11/1985 | Moore | 604/294 |
| 4,593,690 | 6/1986 | Sheridan et al. | 604/281 |
| 4,629,456 | 12/1986 | Edwards | 604/294 |

FOREIGN PATENT DOCUMENTS 1308908  3/1973  United Kingdom ................. 604/294

OTHER PUBLICATIONS

"Creating Smaller Eyedrops by Reducing Eyedropper Tip Dimensions", Brown, et al., *American Journal of Opthalmology*, 99: 460–164, (1985).
Consolidated Plastics Advertisement.
G. Sheldon, "Self-Administration of Eyedrops", Ophthalmic Surgery, vol. 19, p. 393, May, 1987.

*Primary Examiner*—Kyle L. Howell
*Assistant Examiner*—John P. Lacyk
*Attorney, Agent, or Firm*—Fish & Richardson

[57] ABSTRACT

This invention features a bottle for dispensing liquids to an eye. The bottle preferably comprises sterile liquid, has tube portions extending into and out of the bottle, with the outer portion of this tube being flexible, and lying at an acute angle to the axis of the bottle.

7 Claims, 1 Drawing Sheet

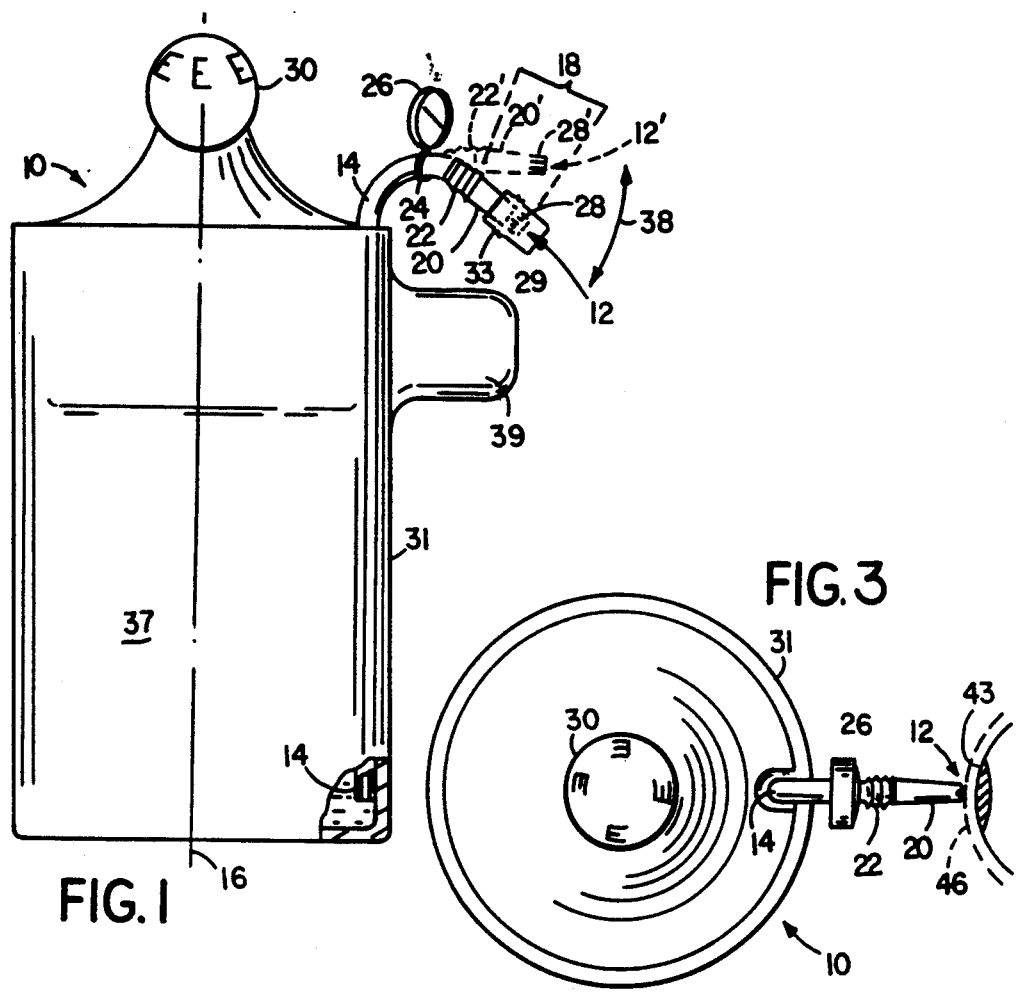
FIG. 3
FIG. 1
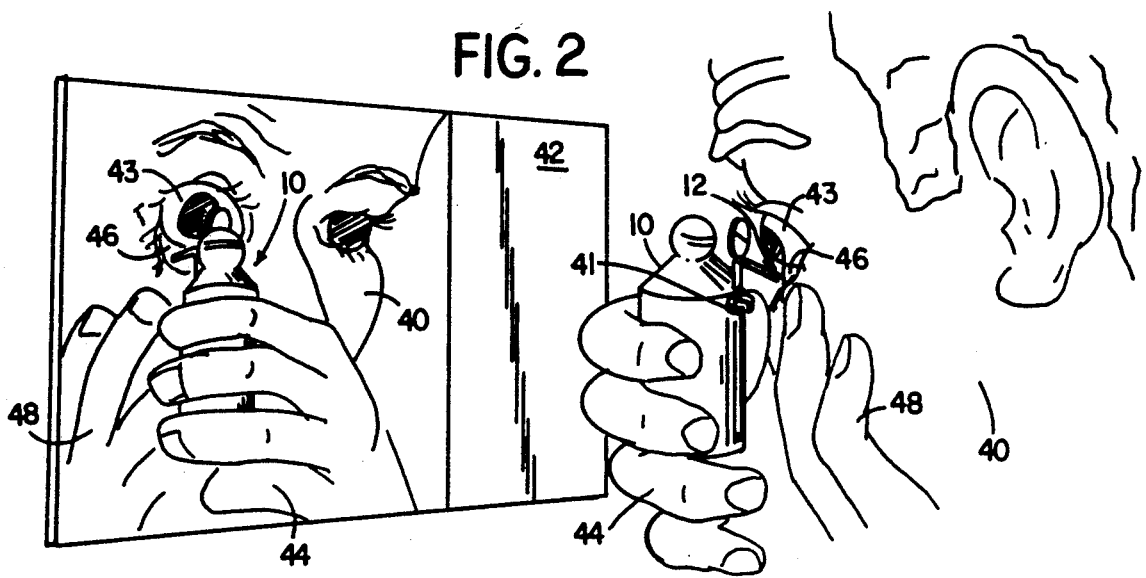
FIG. 2

EYE BOTTLE

This is a continuation of co-pending application Ser. No. 016,538 filed on Feb. 19, 1987 now abandoned.

BACKGROUND OF THE INVENTION

This invention relates to dispensing liquids to human eyes.

Human eyes frequently need to have a medicine, water, or a buffered fluid administered to them. For example, lubricating fluid is needed when an eye is covered by a contact lens for an extended time; and medicinal solutions are required for treatment of infections or diseases, such as glaucoma. It is also necessary to irrigate eyes with a saline solution when they have been contacted with a harmful agent. For example, in some laboratory accidents, an acid or alkali may splash into an eye, and must immediately be diluted and washed away.

German patent 3,035,211 describes an instrument for dispensing an irrigating solution to an eye. The instrument is preferably held on a flat surface with the person leaning over it. Irrigating solution is caused to enter a receptacle in which an eye is positioned, and spent liquid is drained away.

Costello (1970, U.S. Pat. No. 3,506,001) describes a device for spraying an eye with a medicated liquid. This device has a mirror positioned so that the user can line up an eye with the spraying tube.

Strauss (1932, U.S. Pat. No. 1,855,653) describes an eye dropper having a tube extending through a glass bottle containing liquid. A bulb at one end of the tube is squeezed to cause the liquid to be dispensed from the other end.

It is common for people who wear contact lenses or who have ocular diseases to dispense eye drops using a simple plastic bottle having a small hole at one end. In order to get a drop into an eye, the user must tip his head back to bring the surface of the eye to an almost horizontal position.

SUMMARY OF THE INVENTION

In a first aspect, the invention features a plastically deformable bottle for dispensing a liquid into an eye of a human. The bottle has a first tube extending into it having a pathway communicating with an external flexible open-ended tube extending outwardly from the bottle, whereby squeezing the bottle to deform it causes the liquid to pass through the first tube and out the end of the external tube, the flexible tube being capable of being bent by a moving force into a desired position, and remaining in this position after the moving force has ceased.

In preferred embodiments, the flexible tube has a corrugated region; the bottle includes a target and lens to aid in positioning it near the eye; and the bottle further includes a clip for securing the flexible tube against the bottle when not in use.

In a second aspect the invention features a plastically deformable polymeric bottle for dispensing a liquid to an eye of a human, the bottle comprising sterile liquid and being sealed from the external environment. The bottle also comprises a tube extending into the bottle and from the bottle.

In preferred embodiments the bottle has a tube extending from the bottle which is fixed at an acute angle to the longitudinal axis of the bottle.

In a third aspect the invention features a method for dispensing liquid to an eye of a human, the method comprising expelling liquid, from the bottles described, above into a human eye.

My invention provides a bottle which allows sterile liquids to be easily administered by a person to his eyes, without necessitating tipping of the head. The user can observe what he is doing in a mirror, regulate the amount of liquid dispensed, and take care not to add too much liquid to one eye. Further, the container can be easily prevented from contacting the eye, and thus contaminating the container as well as injuring the eye. Since only one hand is needed to regulate liquid flow from the device, the other hand can be used to hold the eye open. The device can also be used to irrigate an eye with a stream of sterile or non-sterile liquid.

Other features and advantages of the invention will be apparent from the following description of the preferred embodiments thereof and from the claims.

The Figures will first briefly be described.

Drawing

FIG. 1 is a cross section through a bottle of the invention.

FIG. 2 is a diagrammatic representation of the bottle in use.

FIG. 3 is a plan view from the top of the bottle.

DESCRIPTION OF THE PREFERRED EMBODIMENTS

Structure

Referring to FIG. 1, bottle 10 is manufactured from a plastically deformable polymeric material, e.g., polypropylene. Bottle 10 is airtight except at the open end 12 of the external portion of tube 14. Tube 14 passes internally nearly the whole length of bottle 10, running parallel to the longitudinal axis 16 of bottle 10. Between the distal (external) end 20 of tube 14 and the rest of tube 14 is flexible, corrugated region 22 which allows movement of end 18 relative to axis 16 of bottle 10, as shown by arrow 38. Also provided on tube 14 is a groove 24 to which optical lens 26 is removably attached. The removable optical lens is a high plus (converging) lens of sufficient power to allow the image of the target 30 to be appropriately positioned on the patient s retina. The end 12 of tube 14 is threaded and has a narrow bore 28 with a smooth surface, formed of a soft plastic, that is a plastic which is readily deformed and thus less likely to hurt an eye than a normal plastic material. Threaded cap 29, with threads 33, mates with end 12 to form an airtight seal to keep liquid 37 in bottle 10 sterile. Cap 29 is removed when bottle 10 is in use.

Bottle 10 is provided with a colored target 30 on top of the main body 31. Target 30 is molded onto the main body by standard procedure, to keep bottle 10 airtight. Cushion pad 39 is also molded as part of bottle 10 and helps to prevent inadvertant injury to an eye from end 12 while the bottle is being used. The volume of bottle 10 is about 20 ml, but can be from 2.5 ml to 150 ml. The bottle is preferably cylindrical.

Use

Bottle 10 is manufactured and filled with a sterile medical or wash liquid 37 by standard procedure. Liquid 37 remains sterile until cap 29 is removed. Contamination of liquid 37 is prevented by the replacement of cap 29 immediately after use.

Referring to FIGS. 2 and 3, to administer one or more drops of liquid 37 from bottle 10, the user adjusts the angle of the flexible portion of tube 14, as shown by arrow 38, to an angle suitable for him. This causes movement of each component 12, 20, 22, and 28 to a position shown as 12', 20', 22', and 28', respectively. The person applies a moving force (e.g., by pushing the tube with a finger) to tube 14, and moves the tube to the desired position. When he removes this moving force the tube will remain in this position. Preferably the tube tip is colored so that it is easily recognized by the person. Different colors of the tip and target can indicate various medicines, such as miotics, dilators or beta blockers. Once the tip is in position (preferably at an acute angle to axis 16, i.e., at an angle less than 90° to the axis) the person may either use a mirror (FIG. 2) to line the nozzle up with one eye, or may use the lens 26 (FIG. 3) to focus on the letters on target 30. With practice a person can use this bottle without need for a mirror. Cushion pad 39 prevents nozzle 12 from being pushed too far into an eye of the user, although the fingers of the hand holding the bottle may also serve this function. Liquid 37 is pushed up tube 14, out of end 12, and into the eye by gently squeezing the bottle.

Referring to FIG. 2, user 40 approaches mirror 42 and holds bottle 10 close to one eye 43 with one hand 44 such that end 12 is positioned just above one lower eyelid 46. The other hand 48 is used to pull eyelid 46 down, thus exposing the surface which normally contacts eye 43 forming a small space or pouch, between the eyelid surface and the eye. By squeezing bottle 10 one or more drops are allowed to fall onto the inner eyelid surface 46. The eyelid is then released and the drops dispersed by blinking.

Alternatively, referring to FIG. 3, when no mirror is available, a person can learn to use lens 26 to focus on the letters on target 30. (The position of end 12 is previously adjusted, using a mirror, such that when the letters are in focus, end 12 of tube 14 is positioned above eyelid 46.) Drops can then be applied as above.

The size of drop administered is controlled by the size of end 12 of tube 14 and by the internal diameter of bore 28, as described by Brown et al., 99 Am. J. of Ophth. 460 (1985).

Other Embodiments

Other embodiments are within the following claims, for example, larger versions of bottle 10, up to 150 ml, can be used to irrigate eyes with a continuous flow of liquid. In such bottles end 12 of tube 14 would be wider to allow for the greater flow. Cushion 39 can be replaced with a clip 41 suitable for holding the external tube 18 close to the outer perimeter of bottle 10 when not in use. Such a clip is useful for holding tube 18 during storage of bottle 10, for example, in a purse. Snap on caps as well as screw on caps can be used to cover the tube tip. The bottle can have a shape other than cylindrical.

I claim:

1. An eye drop dispenser for dispensing a liquid into an eye of a human, comprising:
    a plastically deformable bottle, said bottle comprising an internal tube portion extending into said bottle, said internal tube portion having a pathway communicating with an external flexible, open-ended tube portion extending outwardly from said bottle,
    said bottle further comprising a protrusion adapted to rest against the face of a human below the eye, and to cooperate with the open end of said external tube portion such that when said protrusion is rested against the face of a human below the eye the open end is located adjacent to the eye, wherein
    squeezing said bottle to deform it causes the liquid in said bottle to pass through said internal tube portion and out the open end of said external tube portion into the eye.

2. The dispenser of claim 1 wherein said protrusion is a soft cushion.

3. The dispenser of claim 1 wherein said flexible tube portion is capable of being bent by a moving force into a desired position, and remaining in this position after said moving force has ceased.

4. An eye drop dispenser for dispensing a liquid into an eye of a human, comprising
    a plastically deformable bottle, said bottle comprising an internal tube portion extending into said bottle, said internal tube portion having a pathway communicating with an external flexible, open-ended tube portion extending outwardly from said bottle; and
    a target coupled to said bottle to aid in positioning said dispenser near the eye; wherein
    said flexible tube portion is bent by a moving force into a desired position, and remains in this position after said moving force has ceased, whereby squeezing said bottle deforms said bottle to cause the liquid in said bottle to pass through said internal tube portion and out the open end of said external tube portion into the eye.

5. The dispenser of claim 4 wherein said bottle further comprises an optical lens opposite said target to aid in positioning said bottle near said eye.

6. An eye drop dispenser for dispensing a liquid into an eye of a human, comprising
    a plastically deformable bottle, said bottle comprising an internal tube portion extending into said bottle, said internal tube portion having a pathway communicating with an external flexible, open-ended tube portion extending outwardly from said bottle; and
    a protrusion adapted to cooperate with the open end of said external tube portion such that when said protrusion is rested against the face of a human below the eye the open end is located adjacent to the eye;
    wherein said flexible tube portion is bent by a moving force into a desired position, and remains in this position after said moving force has ceased, and squeezing said bottle to deform it causes the liquid in said bottle to pass through said internal tube portion and out the open end of said external tube portion into the eye.

7. The dispenser of claim 6 wherein said protrusion is a soft cushion.

* * * * *